ND State

United States Patent [19]
Haubennestel et al.

[11] 4,314,924
[45] Feb. 9, 1982

[54] THIXOTROPIC AGENT FOR USE IN COATING COMPOSITIONS

[75] Inventors: Karlheinz Haubennestel; Rainer Mehren, both of Wesel, Fed. Rep. of Germany

[73] Assignee: Byk-Mallinckrodt Chemische Produkte GmbH, Wessen, Fed. Rep. of Germany

[21] Appl. No.: 42,716

[22] Filed: May 25, 1979

[30] Foreign Application Priority Data

May 26, 1978 [DE] Fed. Rep. of Germany ....... 2822908

[51] Int. Cl.³ .................. C08G 71/02; C08K 5/41; C08K 5/21; C08L 5/24
[52] U.S. Cl. .................. 260/30.6 R; 260/30.8 DS; 260/32.6 NR; 528/57; 528/69
[58] Field of Search .................. 528/57, 69; 260/30.8 DS, 32.6 NR, 30.6 R; 525/459

[56] References Cited

U.S. PATENT DOCUMENTS

| | | | |
|---|---|---|---|
| 3,205,201 | 9/1965 | Friedrich et al. | 528/57 |
| 3,499,858 | 3/1970 | Strassel | 260/30.8 DS |
| 3,715,326 | 2/1973 | Traubel et al. | 528/69 |
| 3,871,911 | 3/1975 | Conacher, Jr. | 528/57 |
| 4,155,894 | 5/1979 | Gojewski et al. | 260/30.8 DS |
| 4,182,828 | 1/1980 | Reischl et al. | 260/30.8 DS |

FOREIGN PATENT DOCUMENTS 345716 7/1972 U.S.S.R. .................. 528/57

OTHER PUBLICATIONS

Chem. Abstracts, vol. 82, 1975, Entry 18740u.

*Primary Examiner*—Joseph L. Schofer
*Assistant Examiner*—Peter F. Kulkosky
*Attorney, Agent, or Firm*—Michael J. Striker

[57] ABSTRACT

Thixotropic compositions comprising a solution of a urea urethane having the formula as hereinafter set out dissolved in a polar aprotic solvent containing 0.1–2.0 mol LiCl per urea group:

R—O—CO—NH—R'—NH—CO—NH—R''—NH—CO—NH—R'—NH—CO—OR wherein R represents $C_nH_{2n+1}-$ or $C_mH_{2m+1}(C_pH_{2p}O)_r-$; n represents an integer having a value of from 4 to 22; m represents an integer having a value of from 1 to 18; p represents an integer having a value of from 2 to 4; and r represents an integer having a value of from 1 to 10.

R' represents

[structures shown]

R'' represents

[structures shown]

$-CH_2-CH_2-$, $-(CH_2)_6-$, $-(CH_2)_{12}-$

The solids content in the aprotic solvent amounts to 10–75 wt. % and preferably to from 40–60 wt. %.

13 Claims, No Drawings

THIXOTROPIC AGENT FOR USE IN COATING COMPOSITIONS

This invention relates to thixotropic compositions based on urea urethanes and more particularly relates to thixotropic compositions adapted for use as coating materials containing as thixotropic agent, a urea urethane.

The known thixotropic agents intended for use in coating compositions such as, for example paints, lacquers, varnishes, overlay compositions and like materials are prepared on the basis of hydrogenated castor oil, organically modified bentonite, hydrophilic silicic acid and metal soaps. The disadvantage of these known compositions lies in that in the solid products, film disturbances take place through seeding and are manifested, for example by matting, dulling, frosting and the like and that in certain lacquer systems, such as vinyl resin lacquers, adhesion difficulties frequently occur.

It is also known to use as thixotropic agents polyamide resins having free amino groups. These substances are built into, i.e. incorporated into the lacquer resin, and, therefore, cannot be subsequently introduced for adjusting or correcting the lacquer, varnish or paint formulation. Moreover, under these conditions, gels are produced which are destroyed by low molecular alcohols.

It is further known that through the reaction of primary or secondary amines with mono- or di-isocyanates, ureas are produced which in situ with the binding agent or with a part of the binding agent possess thixotropy (DE-AS No. 2 359 923 and DE-AS No. 2 360 019).

Modified ureas are according to DE-PS 1 805 693 also suitable for use in the production of thixotropic solvent gels which can then be employed in binding agent formulations for thixotropic purposes.

Still further, there is known from DE-AS No. 1 117 801 that reaction products of mono- or polycarboxylic acids with isocyanates, can be introduced and heated together with alkyd resins for imparting thixotropy to the resulting composition.

The substances which have been disclosed in the aforementioned publications have the disadvantage that the thixotropic effect if it is to be successful takes place by reaction with at least a part of the binding agent or the solvent under conditions wherein the reaction of the starting components has to be carried out in high concentration (>20%) or homogeneous phase with the result that there is formed an insoluble or hardly any more manageable product. Further there come into consideration in this case, industrially and hygienically objectionable amines and isocyanates which additionally because of their high reactivity undergo undesirable reactions with the binding agents or the pigments present in the coating formulation.

It is an object of the instant invention to provide agents possessed of thixotropy.

It is another object of the invention to provide agents possessing a high concentration of thixotropic groups which property, however, is possessed in a latent state.

It is still another object of the invention to provide thixotropic agents in a liquid form.

A further object of the invention is to provide occupational and hygienically unobjectionable thixotropic agents.

Still a further object of the invention is to provide thixotropic agents which can be subsequently introduced into coating compositions wherein their thixotropic properties are manifested and the desired thixotropy brought about.

It is yet another object of the invention to provide coating compositions containing such thixotropic agents.

Yet another object of the invention is a method of manufacturing the aforenoted thixotropic compositions.

These and other objects and advantages of the invention are obtained with the urea urethanes of the invention having the following formula:

R—O—CO—NH—R'—NH—CO—NH—R"—NH—CO—NH—R'—NH—CO—OR wherein R represents $C_nH_{2n+1}-$ or $C_mH_{2m+1}(C_pH_{2p}O)_r-$; n represents an integer having a value of from 4 to 22; m represents an integer having a value of from 1 to 18; p represents an integer having a value of from 2 to 4; and r represents an integer having a value of from 1 to 10.

R' represents

[structural formulas: phenyl-CH$_3$, dimethylphenyl, phenyl-CH$_2$-phenyl, —(CH$_2$)$_6$—]

R" represents

[structural formulas containing diphenylmethane, methyl-substituted diphenylmethane, cyclohexyl-phenyl, cyclohexyl-cyclohexyl with CH$_3$ groups, methylenebenzene derivatives]

—CH$_2$—CH$_2$—, —(CH$_2$)$_6$—, —(CH$_2$)$_{12}$—

The solids content in the aprotic solvent amounts to 10–75 wt. % and preferably to from 40–60 wt. %.

The compositions of the invention are utilized in the form of their solutions in a polar aprotic solvent containing 0.1–2.0 mols LiCl per urea group.

The compositions of the invention as just defined have a solids content of 10–75 wt. % and preferably of from 40–60 wt. %.

If the compositions of the invention are employed in a coating formulation, there can be utilized in place of the polar aprotic solvents, suitable lacquer solvents such as alcohols, KW-mixtures, ketones, esters and the like and there is in this case also formed a gel framework which automatically in low use concentrations remains constant. The sol-gel conversion can if desired be repeatedly effected immaterial to the building up of the gel condition, by thermal or mechanical means (as used herein "thixotropy" means the property of certain gels of becoming fluid on shaking, and coagulating again when left at rest; as, a suspension of ferrous hydroxide. It is explained by the mechanical destruction of the zones (q.v.) of oriented molecules).

As the thixotropic agents having the above set out formula can have different substituents in the urea urethane component, it is possible to adjust their compatibility and tolerance to the particular polarity of the thixotropic coating composition system into which any particular thixotropic agent is to be introduced.

The preparation of the agents of the invention can be suitably or expediently carried out by the application of known methods for reacting mono-hydroxy compounds with di-isocyanates to form mono-isocyanate adducts. These mono-isocyanate adducts are then in accordance with the invention converted into urea urethanes by reaction with a polyamine in an aprotic solvent in the presence of LiCl.

As mono-hydroxy compounds suitable for use in the invention, there come into consideration straight or branched chain aliphatic or cyclic, primary or secondary alcohols having 5-24 carbon atoms as well as alkoxylated derivatives of such mono-hydroxy compounds. Preferably, there are used branched chain alcohols, as therewith any crystallization of the substituted urea urethanes in solution is prevented.

For the reaction of the mono-hydroxy compounds with the di-isocyanate, there come into consideration the commercially available di-isocyanates both of aliphatic and aromatic mixture, such as for instance, 1,6-hexamethylene-di-isocyanate and 4,4-di-isocyanato-diphenylmethane. Especially suitable in the sense of the invention are the known toluylenediisocyanates in their isomeric forms (2,4 and 2,6 isomers).

For the further reaction of the mono-isocyanate adduct formed in the first stage of the reaction there are suitable primary and/or secondary aliphatic, cycloaliphatic or aromatic amines which have at least two amine groups for reacting with the isocyanate, such as 4,4-diamino-diphenylmethane, 3,3-dimethyl-4,4-diaminodiphenylmethane, 2,2-bis(4-aminocyclohexyl)-propane, N,N-dimethyl-4,4-diaminodiphenylmethane, (3-methyl-4-aminocyclohexyl)-(3-methyl-4-aminophenyl)-methane, isomeric xylilenediamine, ethylenediamine, hexamethylenediamine and 1,12-diaminododecane.

Especially suitable are 4,4-diaminodiphenylmethane, 3,3-dimethyl-4,4-diaminodiphenylmethane and xylilenediamine.

For the preparation of the urea urethane solution there are required polar aprotic solvents. Instances of such solvents include dimethylsulfoxide, hexamethylphosphoric acid triamide, N,N-dimethylformamide, N,N,N',N'-tetramethylurea N,N-dimethylacetamide, N-methylpyrrolidone, N-butylpyrrolidone.

By introducing the completely or fully reacted urea urethanes into the thixotropic compositions of the invention, the indicated excess of amines noted in DE-PS 1 805 693 becomes unnecessary. This gives rise to an advantage that in avoiding the excess of amine, the appearance of the industrial and hygienic intolerances are avoided. The compositions of the invention can be introduced directly into the coating compositions where they can serve for gelating the carboxyl group containing bonding agents while not interfering with the components for retarding the oxidative drying of the bonding agent, the pigments and dyes for the coloration of the pain film and the components for effecting the catalyzed condensation required, for instance, for annealing of the particular enamel components in the formulation.

The processes described in DE-AS No. 2 359 923 and DE-AS No. 2 360 019 for achieving thixotropy have all of the aforementioned disadvantages including those associated with and depending on the type of binding agent used and deriving from the presence of an excess of amine or isocyanate as this excess is then available for and does react with the reactive components present in the composition such as, for instance, epoxides, monofunctional alcohols or oximes.

The urea urethanes of the invention possess neither the free isocyanate groups nor the free amino groups so that the user can manufacture industrially and hygienically unobjectionable products and which additionally do not undergo any side reactions with the binding agents, pigments or with any other component present in the coating composition or which are subsequently added to the formulation for the coating composition.

The following examples are provided in order to more fully illustrate the manufacture of the urea urethanes of the invention. The reaction takes place in two stages wherein in the first stage the preparation of the alcohol-di-isocyanate adduct is carried out and wherein in the second stage, the preparation of the urea urethanes is accomplished.

GENERAL PROCEDURE FOR THE MANUFACTURE OF ALL TWELVE OF THE UREA URETHANES SHOWN IN TABLES 1A AND 1B:

1 Mol di-isocyanate is first introduced into the reaction vesel; 1 mol of the corresponding OH-functional compound is then slowly added dropwise and the reaction utilizing the known techniques, is then carried to composition.

In the case of the use of aromatic di-isocyanates, care has to be exercised that the temperature does not exceed 40° C. In the case of the use of aliphatic di-isocyanates, temperatures of about 100° C. are suitable for forming the mono adducts.

In a second reaction vessel ½ mol of the corresponding polyamine and 0.1-2.0 mol, preferably 0.5 mol LiCl are dissolved in the corresponding amount of aprotic solvent and then 1 mol of the isocyanate adduct formed in the first reaction stage is introduced. This reaction takes place exothermally.

There results a viscous, clear, yellow-brown color urea urethane solution having a solids content of between 10 and 75% and preferably of between 40 and 50%.

TABLE 1a

| Example No. | Isocyanate-Monoadduct | | NCO-content | |
|---|---|---|---|---|
| | Diisocyanate | Hydroxy-functional compound | % Theor. | found |
| 1 | Toluylenediisocyanate 65% 2,4-isomer | Isotridecanol | 11.3 | 11.1 |
| 2 | Toluylenediisocyanate 65% 2,4-isomer | 2-Octylodecanol | 8.6 | 8.4 |
| 3 | Toluylenediisocyanate 65% 2,4-isomer | Butyltetraglycol | 9.9 | 9.8 |
| 4 | Toluylenediisocyanate 65% 2,4-isomer | Polyoxyethylene monomethylether MG = 350 | 9.6 | 9.5 |
| 5 | Toluylenediisocyanate 65% 2,4-isomer | 2-Hexyldecanol | 9.6 | 9.5 |
| 6 | Toluylenediisocyanate 65% 2,4-isomer | 2-Hexyldecanol | 9.6 | 9.5 |
| 7 | Toluylenediisocyanate 65% 2,4-isomer | 2-Ethylhexanol | 13.8 | 13.6 |
| 8 | Toluylenediisocyanate 80% 2,4-isomer | 2-Hexyldecanol | 9.6 | 9.5 |
| 9 | Toluylenediisocyanate 65% 2,4-isomer | Isotridecanol | 11.3 | 11.1 |

TABLE 1a-continued

| Example No. | Diisocyanate | Hydroxy-functional compound | NCO-content % Theor. | found |
|---|---|---|---|---|
| 10 | Toluylenediisocyanate 65% 2,4-isomer | Isotridecanol | 11.3 | 11.1 |
| 11 | Hexamethylenediisocyanate | Isotridecanol | 12.4 | 12.0 |
| 12 | Toluylenediisocyanate 65% 2,4-isomer | 2-Hexyldecanol | 9.6 | 9.5 |

TABLE 1b

| Isocyanate mono-adduct No. | Polyamine | Urea urethane LiCl mol/mol NHCO-NH | Aprotic Solvent | Solids |
|---|---|---|---|---|
| 1 | 4,4-diaminodiphenylmethane | 0.5 | N-methyl-2-pyrrolidone | 50 |
| 2 | 3,3'-dimethyl-4,4'-diaminodiphenylmethane | 1.0 | N-methyl-2-pyrrolidone | 40 |
| 3 | 4,4'-diaminodiphenylmethane | 0.5 | N-methyl-2-pyrrolidone | 40 |
| 4 | 4,4'-diaminodiphenylmethane | 0.1 | N-methyl-2-pyrrolidone | 40 |
| 5 | Xylilenediamine 1,3 | 0.5 | N-methyl-2-pyrrolidone | 40 |
| 6 | Hexamethylenediamine | 0.5 | N-methyl-2-pyrrolidone | 30 |
| 7 | 4,4'-diaminodiphenylmethane | 0.5 | N-methyl-2-pyrrolidone | 40 |
| 8 | 4,4'-diaminodiphenylmethane | 0.5 | N-methyl-2-pyrrolidone | 60 |
| 9 | 4,4'-diaminodiphenylmethane | 2.0 | dimethylformamide | 50 |
| 10 | 4,4'-diaminodiphenylmethane | 0.5 | dimethylsulfoxide | 50 |
| 11 | 3,3'-dimethyl-4,4'-diaminodiphenylmethane | 0.5 | N-methyl-2-pyrrolidone | 40 |
| 12 | 3,3'-dimethyl-4,4'-diaminodicyclohexylpropane | 0.5 | N-methyl-2-pyrrolidone | 50 |

The urea urethane solutions obtained in Examples 1–12, were then as has been set out in Table 2 treated for their suitability for forming gels in solvents. According to the polarity of the thixotropic products, these are capable of building gels in various polar solvents.

The urea urethane solutions are utilized in the formulations of products wherein the polarity of the product in relation to the polarity of the binding agent and the solvent is determined, i.e. as is the effectiveness of the composition with respect to its thixotropic properties.

TABLE 2

| | Ethylglycol | Butylglycol | Ethylamylketone | Water | Xylol | Xylol/Isobutanol 1:9 | 50% Xylol 20% n-Butanol 20% Methylglycol 10% Cyclohexanone |
|---|---|---|---|---|---|---|---|
| 1 | Tur. Gel | Tur. Gel | Tur. Gel | — | Tur. Gel | Cl. Gel | Tur. Gel |
| 2 | — | — | Tur. Gel | — | Cl. Gel | Cl. Gel | — |
| 3 | Cl. Gel | Tur. Gel | — | — | — | Tur. Gel | Cl. Gel |
| 4 | Tur. Gel | — | — | Tur. Gel | — | — | — |
| 5 | — | — | Cl. Gel | — | Cl. Gel | Cl. Gel | — |
| 6 | — | — | Cl. Gel | — | Cl. Gel | Cl. Gel | — |
| 7 | Tur. Gel | Tur. Gel | — | — | — | Tur. Gel | Tur. Gel |
| 8 | Tur. Gel | Tur. Gel | Tur. Gel | — | Cl. Gel | Tur. Gel | Tur. Gel |
| 9 | Tur. Gel | Tur. Gel | Tur. Gel | — | Tur. Gel | Tur. Gel | Tur. Gel |
| 10 | Tur. Gel | Tur. Gel | Tur. Gel | — | Tur. Gel | Tur. Gel | Tur. Gel |
| 11 | — | Tur. Gel | — | — | Tur. Gel | Tur. Gel | Tur. Gel |
| 12 | — | — | — | — | Tur. Gel | — | — |

Explanation of Table 2:
Meaning of symbols:
— = no gel
tr. gel = turbid gel
cl. gel = clear gel Two of the formulations of the invention are utilized in two lacquer formulations which are especially suitable for thick layer coating with the objective of providing corrosion protection. The two formulations of the invention correspond to Examples 1 and 5 as set out in Table 1. The lacquer formulation used in the case of Example 1 is a chlorinated rubber lacquer and in the case of Example 2, a vinyl resin lacquer formulation.

The lacquers are formulated as follows:

I Chlorinated Rubber Coating Lacquer
Standard trial with customary thixotropic agent

| (a) Mill charge: | Pergut S 10/Xylol solution (21%) (Bayer) | 20.00 g |
|---|---|---|
| | Plasticizer VP-Kl-2351 (Bayer) | 8.44 g |
| | Plasticizer VP-Kl-2357 (Bayer) | 8.44 g |
| | Thixatrol ST (NL-Industries) | 1.68 g |
| | Ironoxide yellow 415 | 1.12 g |
| | Titaniumdioxide R-KB-2 | 16.84 g |
| | Chromoxidegreen GN | 5.98 g |
| | EWO 473 (BaSO4) | 22.50 g |
| | | 85.00 g |
| | ground in the mill grinder | |
| (b) Lacquer Material: | Pergut S 10/Xylol solution (21%) | 115.00 g |
| | | 200.00 g |

The working in of the hydrogenated castor oil (tradename Thixatrol ST) is not easily carried out, i.e. there are problems and a considerable amount of work and energy are required to be expended in order to form the product having the desired consistency.

The powder-formed product as obtained in step (a) above is then introduced into the Pergut S 10/Xylol-solvent and warmed to 40°–50° C. under conditions wherein a good distribution of the powder product in the liquid is obtained.

The product of the invention according to Example 1 is either charged from the mill at a dosing rate of 0.5 and 1% of the 50% product or when the possibility exists of subsequently using higher shearing forces, the lacquer is charged under stirring together with the solvent.

| II Vinylresin-Coating Lacquer |  |
| --- | --- |
| Standard test with conventional thixotropic system (Hydrogenated castor oil/bentonite) | |
| Solvesso 100 (Esso) | 16.46 g |
| Xylol | 41.14 g |
| Kristall oil 21 (Shell) | 24.68 g |
| Laroflex MP 35 (BASF) | 36.00 g |
| Chlorparaffin 50 | 5.40 g |
| Bentone 38/ATU-Paste (NL-Industries/Byk-Mallinckrodt) | 14.40 g |
| Thixatrol ST (NL-Industries) | 0.72 g |
| TiO₂ R-KB-2 | 25.20 g |
| EWO 473 (BaSO₄) | 10.80 g |
| Zinc white RS | 3.60 g |
| Talc AT 1 | 21.60 g |
| | 200.00 g |

The hydrogenated castor oil must also here be predispersed in the xylol under maintenance of a temperature of between 40°–55° C. and then the other components of the formulation can be then worked in. The product of the invention according to Example 5 is charged to the mill with a dosing rate of 0.5 and 1% of the 40% product and the lacquer then further worked up.

The resulting lacquers are then in each case applied with a doctor wiper blade (Norm: ASTM D 823) and are drawn onto and over the test substitute surface. In the test, the running off of the coating composition with the substrate maintained in a perpendicular position is observed. Thereafter the layer thickness of the coating which has not run off is measured.

The resulting film is also visually inspected for homogeneity or spot formation as a result of seeding. The nature of the adhesion achieved is then determined using a grid slit test (ECCA-Method No. 6) carried out on a glass plate. The results are reported as follows:

| GD 0 = very good adhesion |
| --- |
| GD 5 = very poor adhesion. |

The test results can be seen from Table 3 which follows:

TABLE 3

| | Stage (step) doctor (wiper) running off | Lattice (grid) cut | Visual estimate of the surface |
| --- | --- | --- | --- |
| Chlorinated rubber I | | | |
| Standard formula | 90 μm | GD 3 | Spots-seeding |
| 0.5% Example 1 | 200 μm | GD 1 | Homogeneous |

TABLE 3-continued

| | Stage (step) doctor (wiper) running off | Lattice (grid) cut | Visual estimate of the surface |
| --- | --- | --- | --- |
| 1.0% Example 1 | 350 μm | GD 2 | Homogeneous |
| Vinyl resin II | | | |
| Standard formula | 240 μm | GD 5 | Homogeneous |
| 0.5% Example 5 | 500 μm | GD 1 | Homogeneous |
| 1.0% Example 5 | 500 μm | GD 1 | Homogeneous |

As can be seen by evaluating the data set forth in Table 3 the products according to the invention provide essential advantages to the user of thixotropic coating compositions.

We claim:

1. Thixotropic compositions which manifest thixotropic properties only upon subsequent introduction into coating compositions, comprising urea urethanes of the following formula dissolved in a polar aprotic solvent containing 0.1 to 2.0 mol LiCl per urea group

R—O—CO—NH—R'—NH—CO—NH—R''—NH—CO—NH—R'—NH—CO—OR wherein R represents $C_nH_{2n+1}$— or $C_mH_{2m+1}(C_pH_{2p}O)_r$—; n represents an integer having a value of from 4 to 22; m represents an integer having a value of from 1 to 18; p represents an integer having a value of from 2 to 4; and r represents an integer having a value of from 1 to 10, R' represents

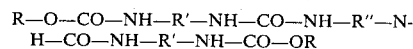

R'' represents

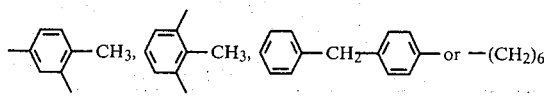

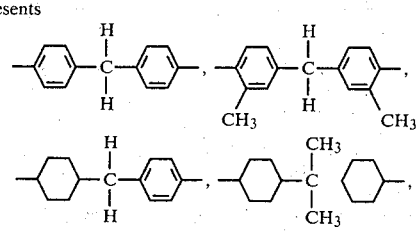

—CH₂—CH₂—, —(CH₂)₆—, or —(CH₂)₁₂—.

2. Thixotropic composition according to claim 1, wherein said aprotic solvent has a solids content of from 10–75 wt. %.

3. Thixotropic composition according to claim 1, wherein said aprotic solvent has a solids content of from 40–60 wt. %.

4. Thixotropic composition according to claim 1, wherein said urea urethane is obtained through reaction of a polyamine with a mono-isocyanate in a polar aprotic solvent in the presence of LiCl.

5. Thixotropic composition according to claim 4, wherein said mono-isocyanate is formed by reaction of a monohydroxy compound with a di-isocyanate.

6. Thixotropic composition according to claim 4, wherein as polyamine there is used a primary or secondary aliphatic, cycloaliphatic or aromatic amine which contains at least 2 amino groups capable of reacting with the isocyanate.

7. Thixotropic composition according to claim 1, wherein said solvent is a member selected from the group consisting of dimethylsulfoxide, hexamethylphosphoric acid triamide, N,N-dimethylformamide, N,N,N',N'-tetramethylurea, N,N-dimethylacetamide, N-methylpyrrolidone and N-butylpyrrolidone.

8. Thixotropic composition according to claim 5, wherein said monohydroxy compound is a straight or branched chain aliphatic or cyclic-primary or secondary alcohol containing 5–24 carbon atoms and alkoxylated derivatives of said monohydroxy compound.

9. Thixotropic composition according to claim 5, wherein the di-isocyanate is 1,6-hexamethylendiisocyanate or 4,4-diisocyanatodiphenylmethane.

10. Thixotropic composition according to claim 9, wherein said di-isocyanate is toluylenediisocyanate.

11. Thixotropic composition according to claim 4, wherein said polyamine is a member selected from the group consisting of 4,4-diamino-diphenylmethane, 3,3-dimethyl-4,4-diamino-diphenylmethane, 2,2-bis(4-aminocyclohexyl)-propane, N,N-dimethyl-4,4-diaminodiphenylmethane, (3-methyl-4-aminocyclohexyl)-(3-methyl-4-aminophenyl)-methane, isomeric xylilenediamine, ethylenediamine, hexamethylenediamine and 1,12-diaminododecane.

12. Thixotropic composition according to claim 4, wherein said polyamine is 4,4-diaminediphenylmethane, 3,3-dimethyl-4,4-diamineodiphenylmethane or xylilenediamine.

13. Process for preparing a urea urethane as set out in claim 1, which comprises in a first stage reacting a monohydroxy compound with a di-isocyanate to form a mono-isocyanato adduct and thereafter in a second stage reacting said mono-isocyanato adduct with a polyamine in an aprotic solvent in the presence of LiCl.

* * * * *